United States Patent
Dressler

(10) Patent No.: US 10,792,007 B2
(45) Date of Patent: Oct. 6, 2020

(54) AUTOMATIC POSITIONING OF A RECORDING SYSTEM

(71) Applicant: Siemens Healthcare GmbH, Erlangen (DE)

(72) Inventor: Christian Dressler, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 34 days.

(21) Appl. No.: 16/299,672

(22) Filed: Mar. 12, 2019

(65) Prior Publication Data

US 2019/0282195 A1   Sep. 19, 2019

(30) Foreign Application Priority Data

Mar. 14, 2018   (EP) .................................... 18161773

(51) Int. Cl.
*A61B 6/08* (2006.01)
*A61B 6/00* (2006.01)

(52) U.S. Cl.
CPC ............ *A61B 6/547* (2013.01); *A61B 6/4007* (2013.01); *A61B 6/4441* (2013.01); *A61B 6/469* (2013.01); *A61B 6/488* (2013.01); *A61B 6/583* (2013.01); *A61B 6/588* (2013.01); *A61B 6/466* (2013.01); *A61B 6/587* (2013.01); *A61B 6/589* (2013.01)

(58) Field of Classification Search
CPC ....... A61B 6/4007; A61B 6/587; A61B 6/466; A61B 6/589; A61B 6/583; A61B 6/547
See application file for complete search history.

(56) References Cited

U.S. PATENT DOCUMENTS

2010/0329416 A1   12/2010   Tsujii
2017/0354386 A1*  12/2017   Yu ......................... A61B 6/547

FOREIGN PATENT DOCUMENTS

| DE | 102006055133 A1 | 6/2008 |
| DE | 102012205238 A1 | 10/2013 |
| JP | 2015195970 A | 11/2015 |

OTHER PUBLICATIONS

European Office Action for European Patent Application No. 18161773. 9-1124, dated Oct. 12, 2018.

* cited by examiner

*Primary Examiner* — Don K Wong
(74) *Attorney, Agent, or Firm* — Lempia Summerfield Katz LLC

(57) ABSTRACT

A method and system are provided for the automatic positioning of a recording system with an x-ray detector and an x-ray source with respect to a subarea of an examination object. A x-ray source to examination object distance is calculated from a displacement distance, the relative pixel distance and the known x-ray source to x-ray detector distance. The x-ray source to examination object distance is used for automatic positioning of the recording system.

13 Claims, 3 Drawing Sheets

AUTOMATIC POSITIONING OF A RECORDING SYSTEM

CROSS REFERENCE TO RELATED APPLICATIONS

This application claims the benefit of EP18161773.9, filed on Mar. 14, 2018, which is hereby incorporated by reference in its entirety.

FIELD

Embodiments relate to automatic positioning of a recording system with an x-ray detector and an x-ray source with respect to a subarea of an examination object.

BACKGROUND

The size of an object on a x-ray image is dependent on the distance of the object from the x-ray detector and from the x-ray source as a result of the cone shape of the x-ray radiation. In order to accurately arrive at, for example, center, a specific point or subarea of a patient or examination object, e.g. of a vertebral body of a patient, on the image using a recording system, it is necessary to know the exact distance between the x-ray source and the object (SOD). The recording system may be formed, for example, by a C-arm, to which an x-ray source and an x-ray detector are fastened. If the SOD is unknown, the corresponding point or subarea may not be centered.

An average value may be assumed for the SOD and the motion error accepted so that a centering of a specific point or subarea is carried out inaccurately. Ultrasound sensors or time-of-flight sensors only measure inter alia the distance of the x-ray source from the patient body as such, but not from the desired object or point in the patient body, i.e. a vertebral body for instance. In certain cases, work is carried out using standardized reference objects, e.g. spheres, the size of which is identified to the system, and therefrom distances are determined on an x-ray image.

SUMMARY AND DESCRIPTION

The scope of the present invention is defined solely by the appended claims and is not affected to any degree by the statements within this summary The present embodiments may obviate one or more of the drawbacks or limitations in the related art.

Embodiments provide a method for the positioning of a recording system with an x-ray detector and an x-ray source with respect to a subarea of a patient, that allows for a exact, automatic positioning of subareas.

The automatic positioning of a recording system is provided with an x-ray detector and an x-ray source with respect to a subarea of an examination object. A first image acquisition of the examination object is performed. A user input is accepted with respect to a subarea of interest of the examination object on the first image. The position of the subarea is stored. The recording system is automatically adjusted so that a lift-free displacement results between the recording system and examination object in a plane parallel to the x-ray detector. The displacement distance ($\Delta m$) is stored. A second image is acquired of the examination object and the position of the subarea of interest is determined on the second image. The relative pixel distance ($\Delta d$) between the position of the subarea of interest on the first and on the second image is determined. The x-ray source subarea distance (SOD) is calculated from the displacement distance, the relative pixel distance and the known x-ray source—x-ray detector distance (SDD). The SOD for an automatic positioning of the recording system is calculated for a centering of the subarea with respect to the x-ray detector.

A subarea of the examination object refers to an anatomical object or a cutout from the examination object or a marker point, that fill at most half, in particular less, of an x-ray image. Examples include vertebral bodies or bones or small organs or prominent hollow organs. The user input may be carried out such that a user obtains the first image in displayed form and marks the subarea thereon, e.g. by a mouse click, by a touchscreen, or on a smart device. The corresponding position of the subarea is then stored. A lift-free displacement refers to a displacement in a plane parallel to the x-ray detector without a lift with respect to the x-ray detector/x-ray source, so that the SOD is not changed during the displacement. If the lift is to change, this must be recorded in the calculations. The displacement of the recording system with the resulting displacement between recording system and examination object in a plane parallel to the x-ray detector may be activated automatically, e.g. by a system controller activating the recording system. The subarea may be moved toward the center of the x-ray detector which is carried out e.g. by using an average value for the SOD.

The displacement distance may be output by the recording system or the system controller. To determine the pixel distance, e.g. the center of the subarea or another specific point of the subarea may be assumed, and may be compared with one another on the two images.

The underlying problem that a precise positioning or even centering of a subarea of an examination object is very difficult and leads to inaccurate positioning of the subarea is solved in that the exact x-ray source—subarea distance is determined automatically. If the SOD is known, a precise positioning may be calculated and carried out. The method may be carried out without additional reference objects during the normal clinical procedure and even during an intervention on the patient. The result is precise and provides for precise positionings. The method may be carried out in a very simple workflow for the user, in which the user only marks the desired subarea or a point therein. Subsequent to the method, other further subareas disposed in the examination object in the same plane as the subarea may be positioned precisely with respect to the x-ray detector. In the case of a vertebral body as a subarea, adjacent vertebral bodies may also be positioned precisely.

The SOD may be calculated according to the intercept theorem, e.g. the formula $$SOD = SDD \cdot \frac{\Delta m}{\Delta d}.$$

According to an embodiment, the position of the subarea of interest on the second image is determined automatically by an algorithm for image recognition or edge detection or object recognition. The method may be automated almost completely, and as a result may proceed quickly and faultlessly.

According to an embodiment, the position of the subarea of interest on the second image is determined by accepting a further user input that may be useful if an automatic recognition of the desired subarea or point is hampered or brings about a false result.

According to an embodiment, the further positioning of the recording system includes a positioning of the subarea of interest in the center of the x-ray detector. With the present SOD, the positioning may be calculated that further displacement the recording system requires to move the subarea into the center and the displacement may then be implemented.

According to an embodiment, the method is repeated as soon as a change in respect of a further subarea of interest takes place. Since another subarea within the patient, that is not disposed in the same plane, changes the SOD, it may be necessary to repeat the method in order again to be able to provide an exact automatic positioning of the recording system. The same also applies when the patient on the patient couch experiences a lift in respect of the plane.

Embodiments include an x-ray imaging system for carrying out the method, including a recording system with an x-ray source and an x-ray detector, a system controller for automatically activating the x-ray imaging system, an image processing unit for processing x-ray images, an input unit for accepting user inputs, a calculation unit, an image output unit and a storage unit. The x-ray imaging system may be formed by a mobile C-arm x-ray system.

DETAILED DESCRIPTION

Figure 1:
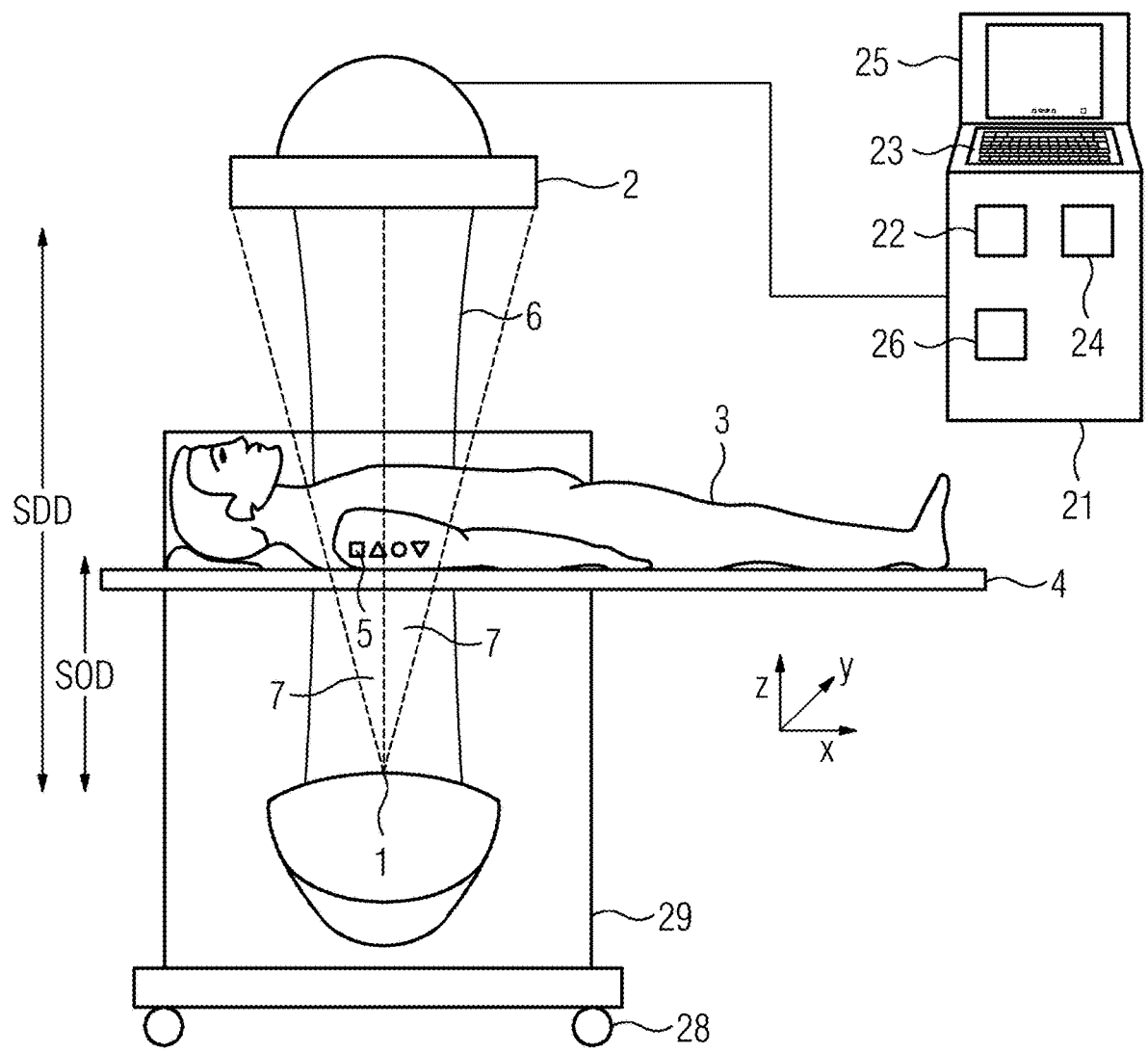
FIG. 1 depicts a view of an x-ray imaging system according to an embodiment.

FIG. 1 depicts a x-ray imaging system 27 with a recording system in the form of a C-arm 6 with an x-ray source 1 and an x-ray detector 2. The x-ray imaging system also includes a system controller 21, that activates the functions of the x-ray imaging system, e.g. the emission of x-ray radiation, the image acquisition, etc. FIG. 1 further depicts an image processing unit 22 for processing x-ray images, a calculation unit 24 for calculating data, a storage unit for storing data and a display unit 25 in the form of a monitor and an input unit 23 in the form of a keyboard and mouse. Alternatively, or in addition, touchscreens or smart devices may also be available for a display and input.

The C-arm 6 is movably fastened to a device trolley 29, for instance, and may be adjusted or moved orbitally and horizontally, for example. The device trolley 29 with the C-arm 6 may be moved manually or automatically by rollers 28.

A patient 3 illuminated by the x-ray radiation in the form of a cone beam 7 lies on a patient couch 4 as an examination object. The shortest possible distance between the x-ray source 1 and the x-ray detector 2, for example, the perpendicular from the x-ray source 1 to the x-ray detector 2, is referred to as x-ray source—x-ray detector distance (SDD). For an automatic positioning of a subarea 5, e.g. of a vertebral body, of the patient 3, the x-ray imaging system 27 is configured to carry out a method. Within the scope of the method, the precise distance between the x-ray source and the subarea of interest (SOD) is determined and is used for the positioning. To display the geometric associations more precisely, a coordinate system xyz is shown, wherein the z-axis is parallel to the SDD and the x-axis and the y-axis cover a plane parallel to the x-ray detector. The problem solved by the method includes the distance between the x-ray source and the patient being easily measurable, but the distance from a subarea of the patient (SOD), for which the plane in which the patient is disposed is not so easily detectable, is very difficult.

Figure 2:
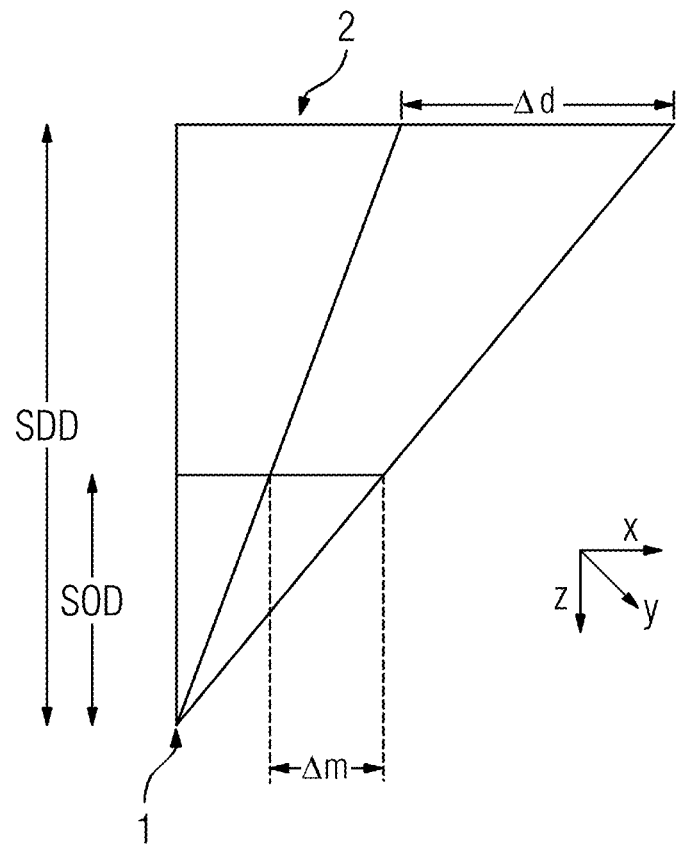
FIG. 2 depicts a view of the geometric associations relating to determining a SOD according to an embodiment.

The geometric associations are depicted again enlarged in FIG. 2. The SOD may be determined from the SDD, a displacement distance $\Delta m$ and a pixel distance $\Delta d$ by the intercept theorem:

$$SOD = SDD \cdot \frac{\Delta m}{\Delta d}$$

Figure 4:
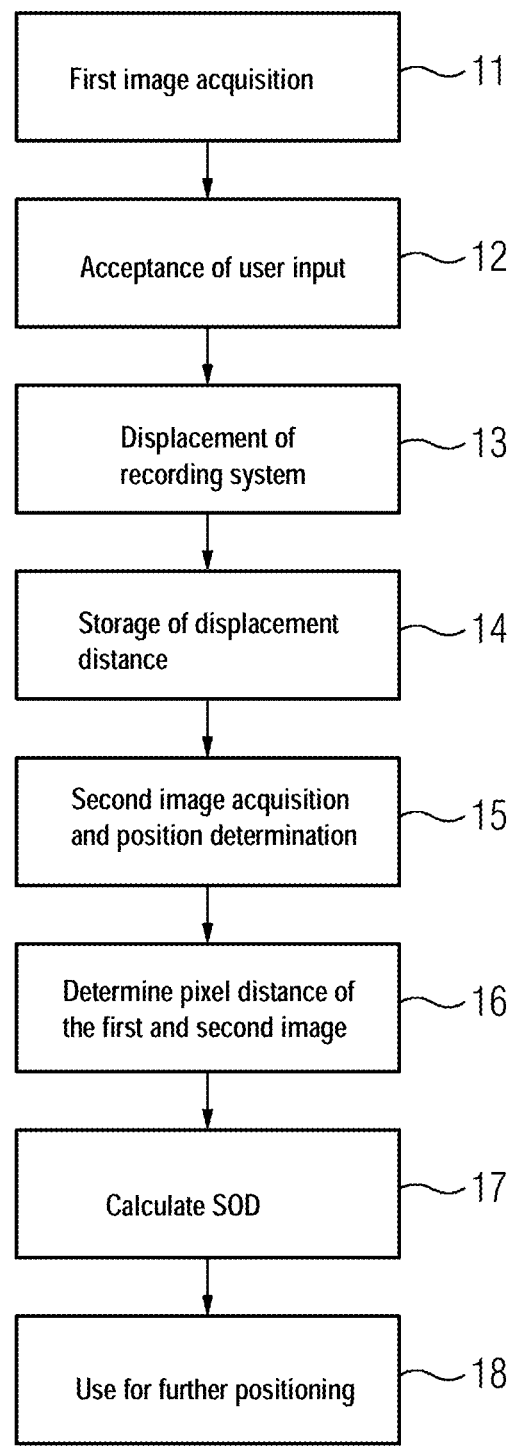
FIG. 4 depicts a flowchart of the method according to an embodiment.

The method is described below in FIG. 4, where a calibration takes place in respect of the SOD and a positioning may then take place on the basis of the calibration.

Figure 3:
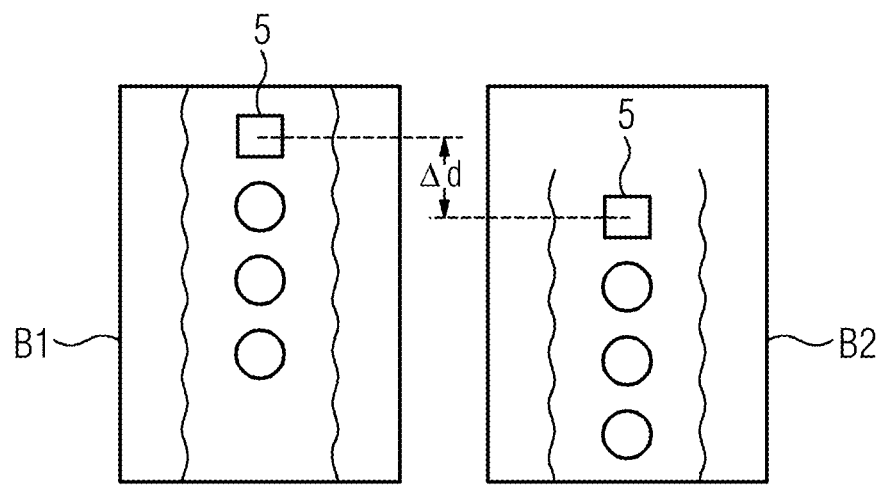
FIG. 3 depicts a view of the two x-ray images with a subarea of interest mapped thereupon according to an embodiment.

A first x-ray image B1 (see also FIG. 3) of the examination object is acquired in a first act 11 and then preferably shown on a display unit 25. In a second act 12, a user input in respect of a subarea 5 of interest on the x-ray image B1 is then accepted and stored. The user may mark the subarea or a point thereupon using the input unit 23. A touchscreen may be used, on which the user marks the corresponding positions directly on the x-ray image shown.

In a third act 13, the recording system is adjusted automatically such that a lift-free displacement by a displacement distance $\Delta m$ between the recording system and examination object results in a plane parallel to the x-ray detector. The adjustment may be formed by a simple translation of the x-ray imaging system or movement of the C-arm in the x-direction and/or y-direction, e.g. along the patient. Adjustments of this type are known and may be activated easily. For example, the displacement may be activated automatically, such that the system controller firstly assumes an estimated SOD, a SOD determined by measurements such as ToF, laser triangulation or ultrasound or an average SOD and attempts are made on the basis of the approximated SOD to center the subarea of interest with respect to the x-ray detector. A preset standard value may also be used for a displacement, for instance.

In a fourth act 14, the absolute displacement distance is stored, that may be taken from encoders in a hinge of the recording system or the rollers/wheels of the device trolley or queried by the system controller.

In a fifth act 15, a second x-ray image B2 is recorded and the position of the subarea or point of interest is determined on this second x-ray image B2. The position determination may be carried out by an object recognition algorithm or an algorithm for image recognition or edge detection, for instance. Alternatively, or in addition, a further user input with respect to the subarea 5 may be accepted. In a sixth act 16, the position of the subarea 5 on the first x-ray image B1 and the second x-ray image B2 is compared and the absolute pixel distance $\Delta d$ in the direction of the displacement is determined, e.g. by the image processing unit in combination with the calculation unit. This is depicted schematically in FIG. 3. From the now known values for the SSD, the pixel distance $\Delta d$ and the displacement distance $\Delta m$, in a seventh act 17 the SOD is calculated by the intercept theorem, e.g.

by the calculation unit. In an eighth act 18, the SOD may be used for a precise positioning of the subarea, e.g. for a positioning of the subarea in the center of the x-ray detector or an x-ray image. The SOD is used to calculate to where the recording system has to be adjusted in order to center the subarea, and the adjustment is implemented by the system controller.

The workflow by the method is as follows: the patient is positioned on the patient couch, the recording system is positioned and the method is started. The first x-ray image is indicated to the user on a touchscreen, for example, and the user marks the subarea of interest. The further steps run automatically, so that at the end of the method, the subarea of interest selected by the user is positioned in a centered manner in respect of the x-ray detector.

Embodiments include a method for the automatic positioning of a recording system with an x-ray detector and an x-ray source with respect to a subarea of an examination object, including the following steps: First image acquisition of the examination object, acceptance of a user input with respect to a subarea of interest of the examination object on the first image and storage of the position of the subarea; automatic adjustment of the recording system such that a lift-free displacement between the recording system and examination object results in a plane parallel to the x-ray detector, storage of the displacement distance ($\Delta m$), second image acquisition of the examination object and determination of the position of the subarea of interest on the second image, determination of the relative pixel distance ($\Delta d$) between the position of the subarea of interest on the first and on the second image; calculation of the SOD (x-ray source—examination object distance) from the displacement distance, the relative pixel distance and the known SDD (x-ray source—x-ray detector distance), and use of the SOD for an automatic positioning of the recording system. The SOD is calculated according to the formula $$SOD = SDD \cdot \frac{\Delta m}{\Delta d}.$$

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for the automatic positioning of a recording system with an x-ray detector and an x-ray source with respect to a subarea of an examination object, the method comprising:

acquiring a first image of the examination object;

accepting a user input with respect to a subarea of interest of the examination object on the first image and storage of the position of the subarea;

adjusting, automatically, of the recording system such that a lift-free displacement between the recording system and examination object results in a plane parallel to the x-ray detector;

storing a displacement distance;

acquiring a second image of the examination object;

determining the position of the subarea of interest on the second image;

determining a relative pixel distance between the position of the subarea of interest on the first and on the second image;

calculating an x-ray source to examination object distance from the displacement distance, the relative pixel distance and the known x-ray source to x-ray detector distance; and using the x-ray source to examination object distance for an automatic positioning of the recording system.

2. The method of claim 1, wherein the x-ray source to examination object distance is calculated according to the formula:

x-ray source to examination object distance = x-ray source to x-ray detector distance $\times \frac{\text{displacement distance}}{\text{relative pixel distance}}$.

3. The method of claim 1, wherein the further positioning of the recording system comprises a positioning of the subarea of interest in the center of the x-ray detector.

4. The method of claim 1, wherein the position of the subarea of interest on the second image is determined automatically by image recognition or edge detection or object recognition.

5. The method of claim 1, wherein the method is repeated as soon as a change in respect of a further subarea of interest takes place.

6. The method of claim 1, wherein the position of the subarea of interest on the second image is determined by accepting a further user input.

7. An x-ray imaging system comprising:

a recording system comprising an x-ray source and x-ray detector configured to acquire a first image of an examination object and a second image of an examination object;

a system controller configured to automatically activate the x-ray imaging system and adjust automatically the recording system such that a lift-free displacement between the recording system and examination object results in a plane parallel to the x-ray detector;

an image processing unit configured to determine the position of the subarea of interest on the second image and determine a relative pixel distance between the position of the subarea of interest on the first and on the second image;

an input unit configured to accept a user input with respect to a subarea of interest of the examination object on the first image and storage of the position of the subarea; and a calculation unit configured to calculate an x-ray source to examination object distance from the displacement distance, the relative pixel distance and the known x-ray source to x-ray detector distance;

wherein the x-ray source to examination object distance is used for an automatic positioning of the recording system.

8. The x-ray imaging system of claim 7, wherein the x-ray imaging system is a mobile C-arm x-ray system.

9. The x-ray imaging system of claim 7, wherein the x-ray source to examination object distance is calculated according to the formula:

$$\text{x-ray source to examination object distance} = \text{x-ray source to x-ray detector distance} \times \frac{\text{displacement distance}}{\text{relative pixel distance}}.$$

10. The x-ray imaging system of claim 7, wherein the further positioning of the recording system comprises a positioning of the subarea of interest in the center of the x-ray detector.

11. The x-ray imaging system of claim 7, wherein the position of the subarea of interest on the second image is determined automatically by image recognition or edge detection or object recognition.

12. The x-ray imaging system of claim 7, wherein the method is repeated as soon as a change in respect of a further subarea of interest takes place.

13. The x-ray imaging system of claim 7, wherein the position of the subarea of interest on the second image is determined by accepting a further user input.

* * * * *